United States Patent [19]

Friese et al.

[11] 4,113,083

[45] Sep. 12, 1978

[54] APPARATUS FOR TRANSFERRING A DEFORMABLE CYLINDRICAL WORK PIECE FROM ONE WORK STATION TO ANOTHER

[75] Inventors: Axel Friese, Wuppertal, Fed. Rep. of Germany; Stefan Simon, Moedling, Austria

[73] Assignee: Dr. Carl Hahn G.m.b.H., Dusseldorf, Fed. Rep. of Germany

[21] Appl. No.: 731,954

[22] Filed: Oct. 13, 1976

[30] Foreign Application Priority Data

Oct. 15, 1975 [DE] Fed. Rep. of Germany ....... 2546245

[51] Int. Cl.² .............................................. B65G 29/00
[52] U.S. Cl. ..................................... 198/480; 198/482; 198/656; 214/1 BD
[58] Field of Search ................... 214/1 R, 1 BD, 1 B; 198/483, 482, 480, 346, 656, 655, 715, 803

[56] References Cited

U.S. PATENT DOCUMENTS

| | | | |
|---|---|---|---|
| 2,984,334 | 5/1961 | Dungfelder et al. | 198/655 |
| 3,316,688 | 5/1967 | Niederer et al. | 198/655 X |
| 3,585,785 | 6/1971 | Smith | 214/1 BD X |
| 3,967,712 | 7/1976 | Waitkins et al. | 198/655 X |

*Primary Examiner*—Frank E. Werner
*Attorney, Agent, or Firm*—Jason Lipow

[57] ABSTRACT

An apparatus is provided for transferring a cylindrical work piece from a first work station to a second work station is provided. The apparatus comprises a transfer element extending substantially in one main plane, and moveable in said plane. The transfer element is provided with a plurality of openings therethrough in which bushes for receiving and transferring work pieces are mounted to be moveable with the transfer element. A device moves each bush into approximate axial alignment with the first work station for receiving a work piece and then in approximate axial alignment with the second work station for discharging a work piece. The bushes are floatingly mounted within the openings to compensate for errors in axial alignment.

10 Claims, 6 Drawing Figures

APPARATUS FOR TRANSFERRING A DEFORMABLE CYLINDRICAL WORK PIECE FROM ONE WORK STATION TO ANOTHER

BACKGROUND OF THE INVENTION

This invention relates to an apparatus for transferring work pieces such as elongated or cylindrical objects, from a first processing station to a second processing station. More specifically, the invention is directed to an apparatus for use in manufacturing catamenial tampons consisting of fibrous material in cylindrical form and, in particular, is concerned with the accurate transfer of partially completed tampons from one work station to another.

As is known, cylindrical coiled wads produced from loosely united fibrous material are compressed to form tampons and, thereafter, are heated to impart shaped retaining properties thereto. One of the difficulties involved in manufacturing such tampons is in transferring the partially completed product from one work station to another, e.g., from a tampon press to a heating device. The tampons, particularly before being heated, are easily deformable and great care must be taken in such a transfer to insure accurate alignment of transferring apparatus or else misshaped tampons will result. The problem is greatly aggravated when this transfer is attempted at high production rates and, in particular, when the transfer is attempted between a relatively cool work station such as, for example, a tampon press and a relatively hot work station such as a shape retaining heated work station. The underlying object of this invention is, therefore, to provide an apparatus for transferring such work pieces between stations while insuring accurate alignment and hence minimum opportunity for product deformation.

SUMMARY OF THE INVENTION

The objects of this invention are accomplished by providing an apparatus for receiving a cylindrical work piece from a first station by axial displacement of said work piece and for then axially displacing said piece into a second station. The apparatus comprises a transfer element extending substantially in one main plane, moveable in said plane, and having a plurality of openings therethrough. Bushes are provided for receiving said work piece, the bushes being mounted within the openings of the transfer element for movement with the transfer element and being arranged within the openings so that the axes of the bushes are transverse to the main plane of the transfer element. Means are provided for moving each of said bushes into approximate axial alignment with the first work station for receiving the work piece and then with approximate axial alignment with the second work station for discharging the work piece. In accordance with this invention, the bushes are floatingly mounted within the openings to compensate for errors in such axial alignment. The apparatus is of course provided with means for axially displacing the work piece into the transfer element and for discharging the work piece into the second station. This method of mounting the bushes has the advantage that small differences in dimensions between delivery and receiving apertures from the various processing stations can readily be compensated for by small movements of the bushes.

In specific embodiments, the bushes are floatingly mounted within the openings for movement in both the axial and radial direction either against the bias of spring mounting means or against the bias of resilient mounting means or against the bias of a combination of spring mounting and resilient mounting means. For example, in the apparatus described above, the spring mounting means may comprise a centering ring affixed to the transfer element around the inner perimeter of the opening. Two conical section rings are slidingly mounted around the bush on either side of the centering ring. A ring of roller members is provided interposed between each conical section ring and the centering ring on either side of the centering ring, the roller members bearing against the respective facing surfaces of each conical section ring and the centering ring. The roller members allow these surfaces to be moved relatively to each other in both the axial and radial direction, i.e., with respect to the axis of the bush. Compression springs are provided at each end of the bush, and bear against the bush on one end of the spring and against the conical section rings on the other end of the spring to urge the conical section rings against the roller members. In this way by choosing compression springs having the same spring characteristics, the bush will be mounted with its center of gravity substantially within the principal plane of the transfer element and held there by the bias of the two springs. At the same time, the bush will be capable of both axial and radial movement against the bias of the springs.

As an alternative, the bushes may be floatingly mounted to move in both the axial and radial direction against the bias of elastomeric resilient mounting means such as, for example, a rubber mounting means. In such an embodiment, a cylindrical sleeve comprising such a resilient material as rubber may be disposed around the bush and between the bush and the inner perimeter of the opening in the transfer element. The sleeve is yieldable to an extent sufficient to allow the bush to move in both the axial and radial direction. In a preferred embodiment, the sleeve is provided with hollow walls which enhance its yieldability and further enhance the ability of the bush to move in the axial and radial direction.

In a still further embodiment, the bushes may be floatingly mounted within each opening so as to move in both the axial and radial direction against the bias of both elastomeric and spring mounting means. An example of such an embodiment may comprise a rigid cylindrical sleeve disposed around the bush and the inner perimeter of the opening. The bush is disposed within the sleeve so as to be able to move axially therein, however, the sleeve is axially affixed to the transfer member. Compression springs are provided at each end of the bush, each bearing at one end of the sring against the bush and at the other end against the sleeve whereby the bush is axially displaceable within the sleeve against the bias of the springs. A resilient ring is provided interposed between the sleeve and the inner perimeter of the openings. The resilient ring is radially displaceable with respect to the axis of the bush and permits the bush and the sleeve assembly together to be radially displaceable within the opening against the bias of the resilient ring.

The floatingly mounted bushes may now be accurately axially aligned with either the first or second work station for accurately transferring a tampon without deformation. To aid in doing this, centering means may be provided for accurately aligning the end surfaces of either of the parts comprising the bushes and the work stations. Such centering means may comprise providing the end face of one of the said parts with a conical centering recess or depression which is adapted to cooperate with centering chamfers in the end face of the other part. It will be understood that either the bush or the work station may be provided with a recess with the other part being provided with a raised centering chamfer. In a preferred embodiment of this invention, means are also provided for urging the floating bushes against the work station prior to receiving and rejecting a work piece. The floating bushes when so urged against the work station and provided with the above described centering means will accurately align with the work station and insure good transfer.

BRIEF DESCRIPTION OF THE DRAWINGS

The invention will be more particularly described by way of example with reference to the accompanying drawings, in which.

DETAILS OF THE INVENTION

Figure 1:
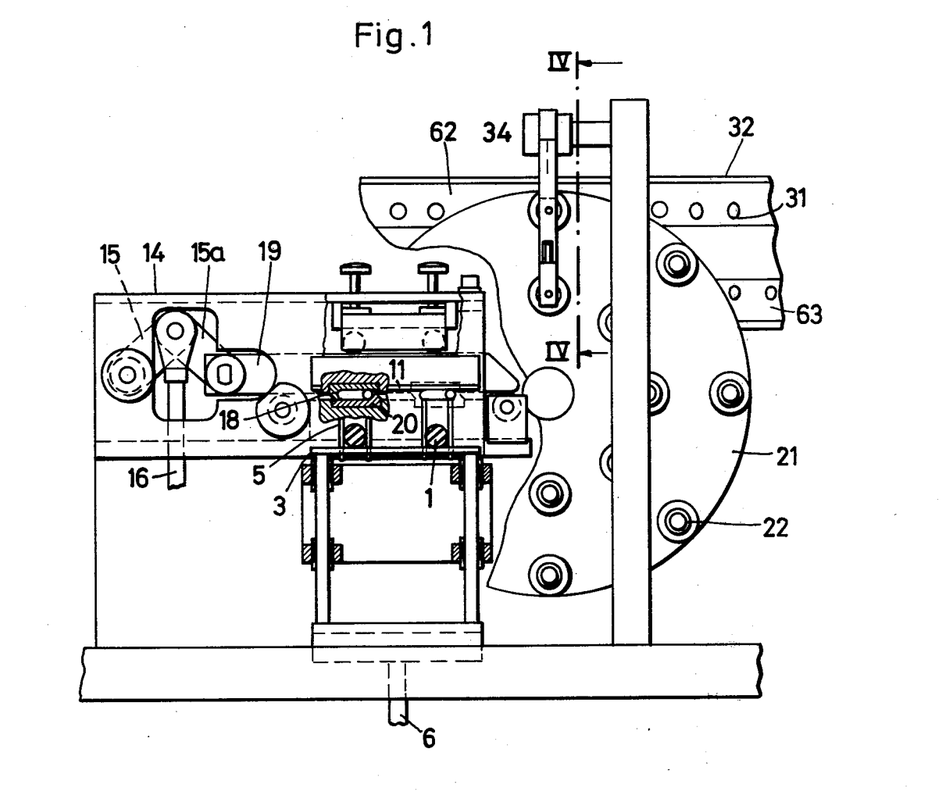
FIG. 1 illustrates, in a sectional view along the line I—I of FIG. 2, a transfer element disposed between a first processing station and a second processing station.
Figure 2:
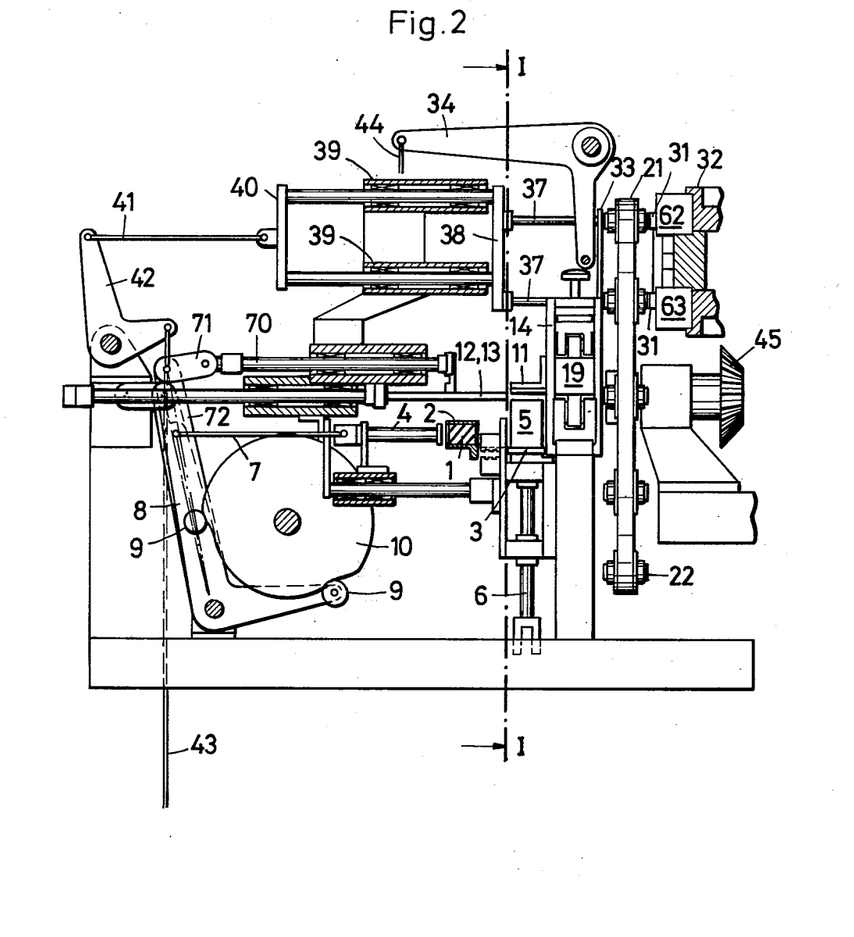
FIG. 2 is a diagrammatic side elevation of the arrangement of FIG. 1.

In the specific embodiment illustrated in FIGS. 1 and 2, substantially cylindrical coiled wads 1 produced by a coiling machine are supplied, by means of conveyor buckets 2 secured to a chain system, to a lifting device 3 mounted in front of a first processing station consisting of a beam press 14. Two wads 1 are shifted at one time from two conveyor buckets 2 of the intermittently stepped-forward conveying system by shifters 4 reciprocating between the side walls of the lifting device 3. The shifters 4 are pivotally connected to a bell-crank lever 8 by way of a push rod 7. Disposed on the lateral surface of the bell-crank lever 8 are rollers 9, which engage a cam disc 10 whose rotational movement brings about the desired displacement adapted to the rate of operation of the machine.

The upward movement of the lifting device 3 is initiated similarly to the movement of the shifter by way of a lifting rod 6 which is connected (though not shown in the drawing) through a lever, a further push rod and a lever system to a roller which is disposed on the lateral surface of the lever and which follows a preset curved path. Shortly before the lifting device 3 reaches the upper position, the wads 1 are pressed flat between a plate of the lifting device and an upper abutment plate 11. The flattened wads are conveyed from the lifting device 3 into the beam press 14 by means of two flat shifters 12 and two round shifters 13 which operate in conformity with the flat shifters 12, the movement necessary for this purpose being transmitted through a push rod 70, a pin-jointed connecting member 71 and rollers (not shown) mounted on a bell-crank lever 72, which engage with a cam disc (also not shown).

In the beam press 14, the flattened wads are pressed into the form of a cylindrical body. The force for the pressing operation of the beam press 14 is exerted, as best viewed in FIG. 1, through a pair of toggle levers 15, 15a, a tie rod 16 and a lever (not shown), on the ends of which there are mounted rollers which are in engagement with the cam path of a cam disc. During the pressing operation, two pressing claws 18 secured to a movable beam 19 are moved in the direction of fixed pressing claws 20.

On completion of the pressing operation, the pressed objects are pushed out, by means of the round shifters 13, into a transfer element, which is in the form of a stepping wheel 21. In accordance with this invention, the transfer element on stepping wheel 21 is provided with a plurality of bushes 22, floatingly mounted in a plurality of opening or apertures 78 (shown in detail in FIGS. 3–6) in the stepping wheel. Two of the bushes 22 provided in the stepping wheel 21 take up two of the pressed objects from the beam press 14 at one time. The bushes 22 of the stepping wheel 21 are so disposed in the apertures 78 of the latter that they lie with their center of gravity substantially in the principal plane of the stepping wheel 21 and are resiliently centered in this position by means of spring elements. This resilient centering makes it possible for the bushes 22 to be moved axially and radially within fixed limits in order to render possible exact alignments with delivery apertures 73 of the beam press 14 and with mould bushes 31 in a second processing station, in the case of this specific embodiment, which consists of a heating turret 32.

Figure 3:
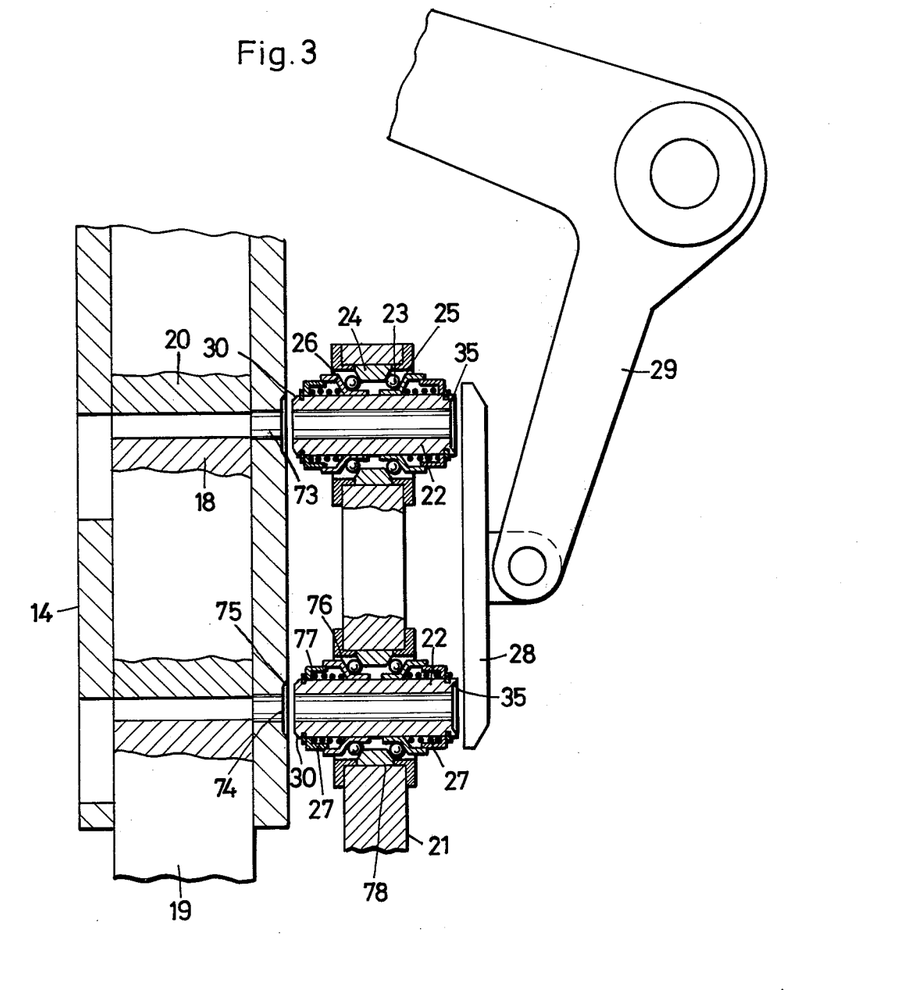
FIG. 3 is a sectional view of a part of the transfer element in association with the first processing station.
Figure 4:
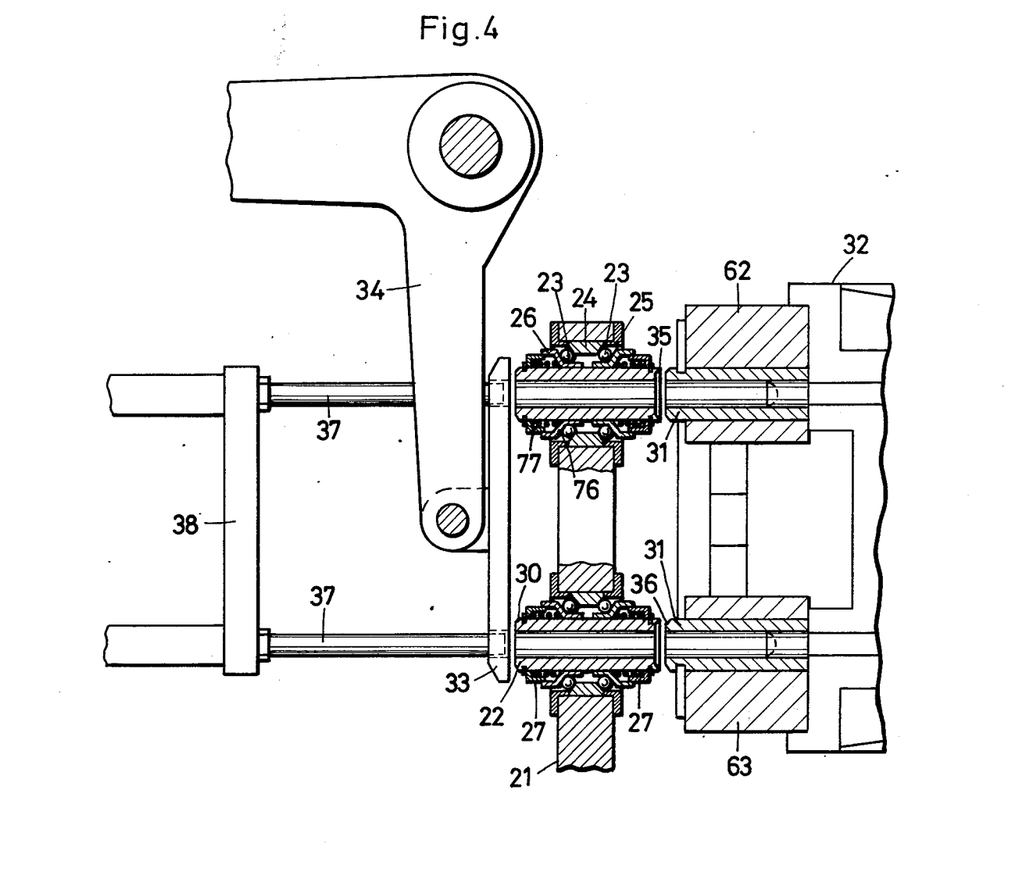
FIG. 4 is a sectional view of a part of the transfer element in association with the second processing station with a first form of construction of the floating bush mounting.

In the form of construction illustrated in FIGS. 3 and 4, an annular shoulder 77 is disposed in the region of the outer ends of each bush 22. There bears against each said annular shoulder 77, one end of a coil compression spring 27 with the other end of the spring bearing against a conical section ring 26. The spring characteristics of the two coil compression springs 27 disposed between the annular shoulder 77 and the conical section ring 26 in each instance are identical. Each ring 26 is so designed to have a coaxial ring section bearing against the bush 22 and further to extend through an outwardly conically flared section 76 to an outer coaxial ring section. Mounted on those faces 25 of the conical sections 76 of the rings 26 which are furthest from the coil compression springs 26, are roller members or balls 23 which in turn bear against corresponding conical surfaces of a centering ring 24 which is provided in each aperture 78 in the stepping wheel 21. There are thus obtained two parallel ring-shaped rows of balls 23 which are held apart by the conical surfaces of the centering ring 24.

As is apparent from FIG. 3, the two associated bushes 22 are pressed axially against the beam press 14 by means of a pressing rail 28 and a lever 29 mounted thereon. During the transfer operation of the pressed articles from the beam press 14 into the stepping wheel 21, the centering of the two bushes 22 in relation to the delivery apertures 73 of the beam press 14 are effected by means of a chamfer 30, which is provided on the outside edge of the bush 22 and with which there is associated a corresponding recess 74 with a centering depression 75 around the delivery apertures 73 of the beam press 14. The lever 29 is concealed in FIG. 1 as it lies in a plane parallel or in the plane of the horizontal diameter of the stepping wheel 21, as it is actuated by mechanisms (not shown) in accordance with the operating rate of the arrangement.

When the pressed articles have been taken up in the bushes 22 of the stepping wheel 21, the centering force exerted by way of the lever 29 and the pressing rail 28 is relieved. The stepping wheel 21 then steps forward through 45° in the clockwise direction. The pressing and transfer cycle is then repeated, the succeeding pair of bushes then being positioned opposite the delivery apertures 73.

After a further step through 45°, the bushes 22 filled with pressed objects have reached a vertical position, in which the pressed objects are transferred into two mould bushes 31 in the heating turret 32 having a plurality of such bushes. (FIGS. 1 and 2.) In order to align the bushes 22 of the stepping wheel 21 coaxially and flush with the mould bushes 31 of the heating turret 32, the bushes 22 are pressed against the end faces of the mould bushes 31 by means of a plate 33 and a lever 34 mounted thereon. In this operation, a centering of the bushes 22 in the mould bushes 31 takes place by way of the centering depression 35 provided in each bush 22, and by way of the chamfer 36 formed on the outside of each mould bush 31.

The movement for the axial displacement of the bushes 22 is initiated by way of a lever 34, a tie rod 44 and a lever (not shown). A cam disc, in engagement with rollers mounted on the end of the latter lever, is actuated in accordance with the rate of operation of the machine and controls the movement of lever 34.

The transfer of the pressed articles from the bushes 22 into the mould bushes 31 takes place, as may be seen from FIGS. 2 and 4, by means of round plungers 37 which are secured to a rail 38 and guided in two round guides 39. The movement is initiated by way of a yoke 40, a push rod 41, a lever 42, a tie rod 43 and a lever (not shown) having rollers mounted on one end, on which a cam disc acts in accordance with the rate of operation of the machine.

The rotational movement is transmitted to the stepping wheel 21 by means of a bevel wheel 45 which is driven intermittently by step-by-step gearing in accordance with the rate of operation of the machine. The double-track heating turret 32 consists substantially of two superimposed rings 62 and 63, each of which has a series of bushes with a number of mould bushes 31 situated at equal intervals around the periphery. The mould bushes 31 are so mounted in the rings 62 and 63 by means of straps as to be axially fixed and to rotate therewith.

Figure 5:
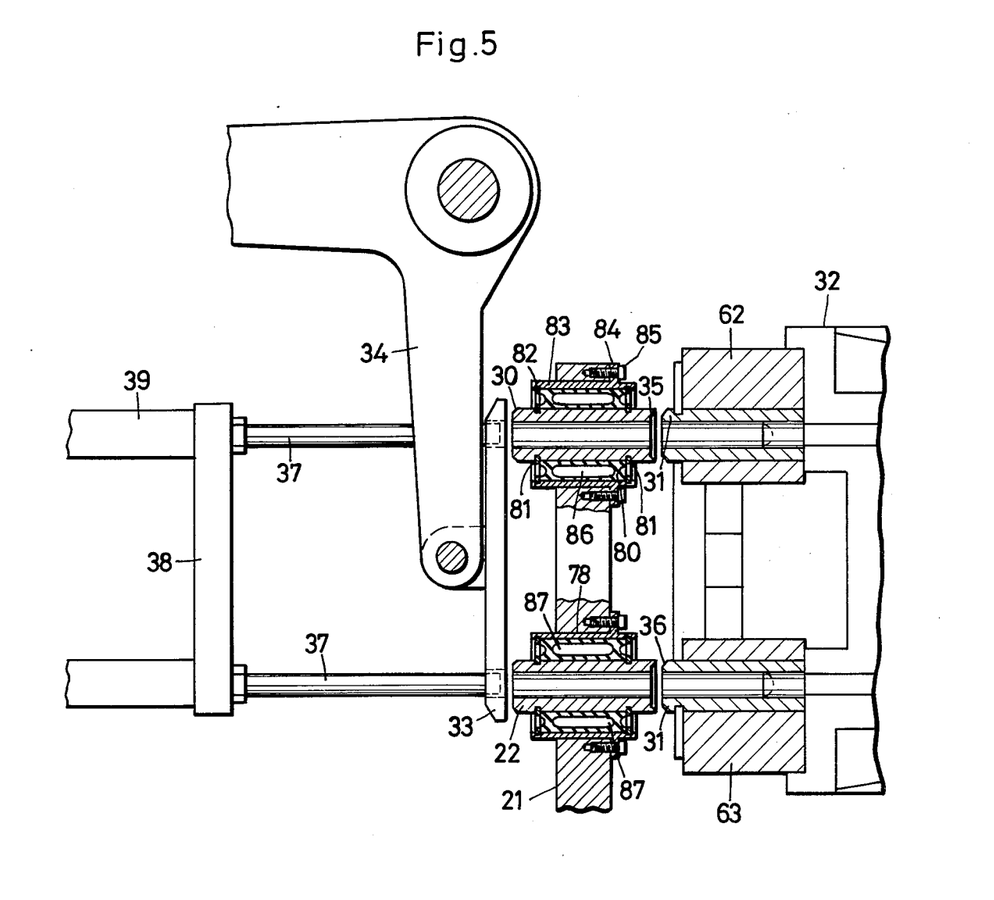
FIG. 5 shows a second form of construction of a floating bush mounting in a view similar to FIG. 4.

In the form of construction illustrated in FIG. 5, the floating mounting of the bushes 22 in the stepping wheel 21 is obtained by means of a sleeve 80 consisting of resilient material, such as rubber or caoutchouc, in which there is defined a ring-shaped cavity 86 extending coaxially with the bush 22 and bounded at its ends by circular surfaces 87. The sleeve 80 is axially fixed to the bush 22 by clips 81. The periphery of the sleeve 80 is surrounded by a thin-walled cylinder 83 which is mounted in the aperture 78 in the stepping wheel 21 and is secured thereto by means of a flange 84 and screws 85. The sleeve 80 is axially fixed in relation to the cylinder 83 by clips 82. The bushes 22 are centered by the centering chamfers and the associated centering depressions as described with reference to FIG. 4.

Figure 6:
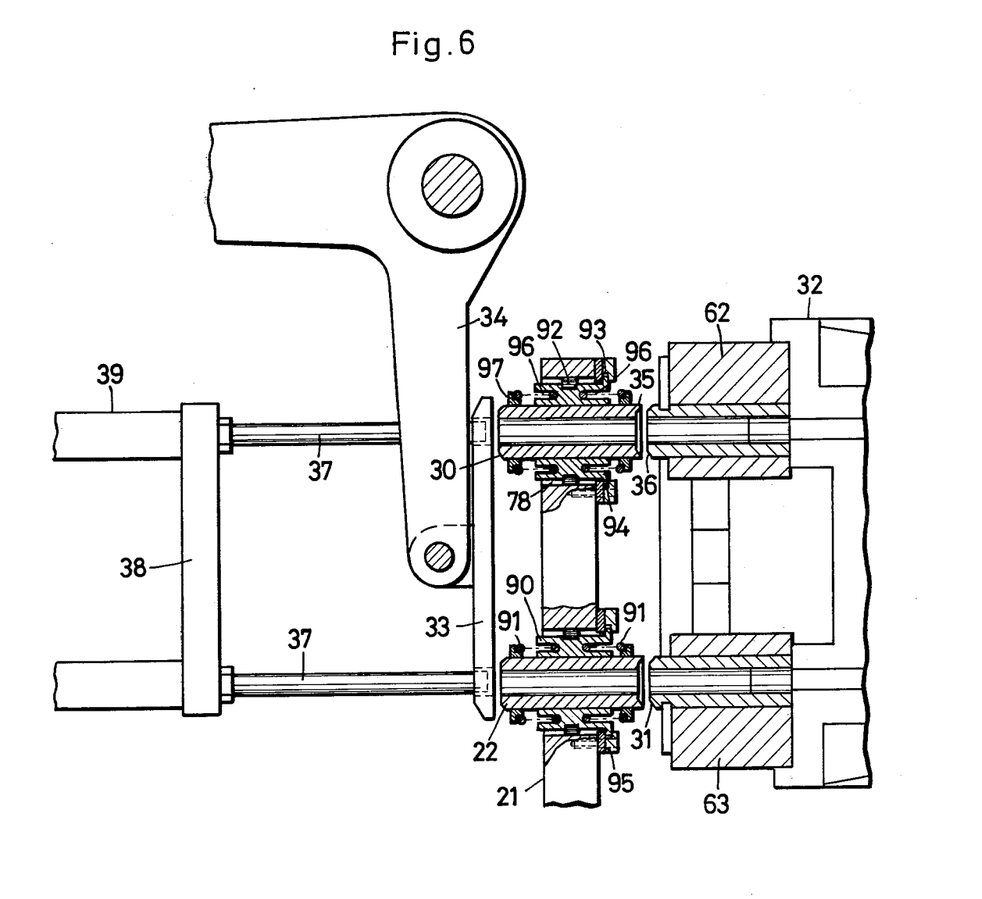
FIG. 6 shows a third form of construction of a floating bush mounting in a view similar to FIG. 4.

In the form of construction illustrated in FIG. 6, each bush 22 is surrounded by a rigid sleeve 90 having, in both end faces, ring-shaped grooves 96 against which there bears coil compression springs 91, which bear, in turn, at their other end, against abutments 97 secured to the bush. Owing to their like spring characteristics, coil compression springs 91 urge the bush 22 into a central position in relation to the stepping wheel 21, so that the center of gravity of the bush is substantially in the principal plane of the stepping wheel 21 and is displaceable against the bias exerted by the springs 91. Situated in an external peripheral groove in each sleeve 90 is a ring 92 consisting of elastic material, preferably rubber, which bears, with freedom of radial movement, against the circular cylindrical inside surface of the aperture 78 in the stepping wheel 21. Sleeve 90 engages the stepping wheel 21, by means of a radial claw 94 in a ring-shaped groove 93 in the inside surface of the aperture 78 so as to be axially non-displaceable, but radially movable. The ring-shaped groove 93 in the illustrted embodiment is formed by applying a shaped element 95 to the stepping wheel 21 and screwing it thereto. In this form of construction, each bush 22 can move axially against the bias of springs 91 and radially, through the spacing defined between the sleeve 90 and the aperture 78, against the bias of the resiliently deformable ring 92, so that the movement necessary for centering is ensured as in the forms of construction shown in FIGS. 3 to 5. The bushes 22 and the associated parts of the processing stations are again provided with corresponding centering chamfers and centering depressions as are shown in these Figures.

What is claimed is:

1. An apparatus for receiving a deformable cylindrical work piece from a first station by axial displacement of said piece and for axially displacing said piece into a second station, comprising:
    a transfer element extending substantially in one main plane and movable in said plane, said transfer element having a plurality of openings therethrough said openings having an inner perimeter;
    bushes for receiving said work piece, said bushes mounted within said openings for movement with said transfer element and with their axes transverse to said main plane;
    means for moving each of said bushes into approximate axial alignment with said first station for receiving a work piece, and for moving said bushes into an approximate axial alignment with said second station for discharging said work piece; and
    said bushes being floatingly mounted within said openings so as to be able to move in both the axial and radial direction to compensate for errors in said alignment;
    said apparatus being provided with means for axially displacing said work piece into said transfer element and means for axially discharging said work piece into said second station.

2. The apparatus of claim 1 wherein each of said bushes is floatingly mounted within each opening to move in both the axial and radial direction against the bias of spring mounting means.

3. The apparatus of claim 2 wherein said spring mounting means comprise:
    a centering ring affixed to the transfer element around the inner perimeter of the opening;
    two conical section rings, slidingly mounted around the bush on either side of the centering ring;
    a ring of roller members, interposed between each conical section ring and the centering ring on either side of said centering ring, said roller members bearing against the respective facing surfaces of each conical section ring and the centering ring while allowing these surfaces to be moved relatively to each other in both the axial and radial direction with respect to the axis of the bush; and compression springs at each end of the bush, bearing against the bush on one end and against each of the conical section rings on the other to urge the conical section rings against the roller members.

4. The apparatus of claim 1 wherein each of said bushes is floatingly mounted within each opening to move in both the axial and radial direction against the bias of elastomeric, resilient mounting means.

5. The apparatus of claim 4 wherein said elastomeric resilient mounting means comprise a cylindrical sleeve deposed around the bush and between said bush and the inner perimeter of the opening, said sleeve being yieldable to an extent sufficient to allow the bush to move in both the axial and radial direction.

6. The apparatus of claim 5 wherein said sleeve is provided with hollow walls to enhace its yieldability.

7. The apparatus of claim 1 wherein each of said bushes is floatingly mounted within each opening to move to both the axial and radial direction against the bias of both elastomeric and spring mounting means.

8. The apparatus of claim 7 wherein said elastomeric and spring mounting means comprise:

a cylindrical sleeve deposed around the bush and between said bush and the inner perimeter of the opening, said bush being disposed within said sleeve to move axially therein, said sleeve being axially affixed to said transfer member;

compression springs at each end of said bush, each bearing at one end against said bush and at the other end against the sleeve whereby said bush is axially displaceable within said sleeve against the bias of said springs; and a resilient ring interposed between said sleeve and the inner perimeter of said openings, said resilient ring being radially displaceable with respect to the axis of the bush permitting said bush and sleeve assembly to be radially displaceable within said opening against the bias of said resilient ring.

9. An apparatus in accordance with claim 1 wherein centering means are provided for accurately aligning end faces of the parts comprising the bushes and the work stations said means comprising:

the end face one of said parts having a conical centering recesses adapted to cooperate with centering chamfers in the end face of the other part.

10. The apparatus of claim 9 wherein means are provided for urging the floating bushes against the work station prior to receiving and rejecting a work piece.

* * * * *